United States Patent
Govari et al.

(10) Patent No.: US 8,521,462 B2
(45) Date of Patent: Aug. 27, 2013

(54) CALIBRATION SYSTEM FOR A PRESSURE-SENSITIVE CATHETER

(75) Inventors: Assaf Govari, Haifa (IL); Yaron Ephrath, Karkur (IL); Andres Claudio Altmann, Haifa (IL)

(73) Assignee: Biosense Webster (Israel), Ltd., Yokneam (IL)

(*) Notice: Subject to any disclaimer, the term of this patent is extended or adjusted under 35 U.S.C. 154(b) by 541 days.

(21) Appl. No.: 12/646,242

(22) Filed: Dec. 23, 2009

(65) Prior Publication Data

US 2011/0153253 A1 Jun. 23, 2011

(51) Int. Cl.
*G01L 1/04* (2006.01)

(52) U.S. Cl.
USPC .............................. 702/104; 702/41; 702/150

(58) Field of Classification Search
USPC .................. 702/85, 98, 104, 41–44, 150, 152, 702/153; 600/463, 407, 424
See application file for complete search history.

(56) References Cited

U.S. PATENT DOCUMENTS

| | | | |
|---|---|---|---|
| 4,764,114 A | 8/1988 | Jeffcoat et al. | |
| 5,391,199 A | 2/1995 | Ben-Haim | |
| 6,239,724 B1 | 5/2001 | Doron et al. | |
| 6,332,089 B1 | 12/2001 | Acker et al. | |
| 6,335,617 B1 | 1/2002 | Osadchy et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,695,808 B2 | 2/2004 | Tom | |
| 6,915,149 B2 | 7/2005 | Ben-Haim | |
| 7,397,364 B2 * | 7/2008 | Govari ..................... | 340/539.12 |
| 8,083,691 B2 * | 12/2011 | Goldenberg et al. ......... | 600/587 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2004/0254458 A1 | 12/2004 | Govari | |
| 2007/0021742 A1 | 1/2007 | Viswanathan | |
| 2007/0060847 A1 | 3/2007 | Leo et al. | |
| 2007/0100332 A1 | 5/2007 | Paul et al. | |

(Continued)

FOREIGN PATENT DOCUMENTS

| | | |
|---|---|---|
| EP | 2047797 A2 | 4/2009 |
| JP | 2005/345215 | 12/2005 |

(Continued)

OTHER PUBLICATIONS

European Search Report, dated Mar. 28, 2011, for European Pat. Appln. No. 10252191.1.
European Search Report, dated Sep. 15, 2011, for European Pat. Appln. No. 11169251.

(Continued)

*Primary Examiner* — Manuel L Barbee
(74) *Attorney, Agent, or Firm* — William A. Schoeneman (57) ABSTRACT

A calibration apparatus includes a fixture, which is coupled to accept a probe so that a distal tip of the probe presses against a point in the fixture and produces first measurements indicative of a deformation of the distal tip relative to a distal end of the probe, in response to pressure exerted on the distal tip. A sensing device is coupled to the fixture and is configured to produce second measurements of a mechanical force exerted by the distal tip against the point. A calibration processor is configured to receive the first measurements from the probe, to receive the second measurements from the sensing device and to compute, based on the first and second measurements, one or more calibration coefficients for assessing the pressure as a function of the first measurements.

19 Claims, 5 Drawing Sheets

(56) References Cited

U.S. PATENT DOCUMENTS

2007/0151391 A1 7/2007 Larkin et al.
2008/0065111 A1 3/2008 Blumenkranz et al.
2008/0183075 A1 7/2008 Govari et al.
2009/0093806 A1 4/2009 Govari et al.
2009/0138007 A1 5/2009 Govari et al.

FOREIGN PATENT DOCUMENTS

WO    WO 96/05768    2/1996
WO    WO 97/29678    8/1997
WO    WO 2007/098494 A1    8/2007

OTHER PUBLICATIONS

Instron Marketing Brochure, "Medical Device Testing Systems", Instron 2007 http://web.archive.org/web/20080318092822/http://www.instron.com.tr/wa/library/streamfile.aspx?doc=1678&download=true.

Instron, "Series 3300 Load Frames, Reference Manual Equipment", Instron, pp. 1-5 and 1-10, 2004.

Peirs, J. et al., "Design of an Optical Force Sensor for Force Feedback During Minimally Invasive Robotic Surgery", Eurosensors XVII, 2003, http://www.mech.kuleuven.be/micro/pub/medic/Paper_Eurosensors_2003_MIS_senor_extended.pdf.

* cited by examiner

CALIBRATION SYSTEM FOR A PRESSURE-SENSITIVE CATHETER

FIELD OF THE INVENTION

The present invention relates generally to invasive probes, and specifically to calibrating pressure sensors in invasive probes.

BACKGROUND

A wide range of medical procedures involve placing objects, such as sensors, tubes, catheters, dispensing devices and implants, within the body. Position sensing systems have been developed for tracking such objects. Magnetic position sensing is one of the methods known in the art. In magnetic position sensing, magnetic field generators are typically placed at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

When placing a probe within the body, it may be desirable to have the distal tip of the probe in direct contact with body tissue. The contact can be verified, for example, by measuring the contact pressure between the distal tip and the body tissue. U.S. Patent Application Publications 2007/0100332 and 2009/0093806, whose disclosures are incorporated herein by reference, describe methods of sensing contact pressure between the distal tip of a catheter and tissue in a body cavity using a force sensor embedded in the catheter. The distal tip of the catheter is coupled to the distal end of the catheter insertion tube by a resilient member, such as a spring, which deforms in response to force exerted on the distal tip when it presses against endocardial tissue. A magnetic position sensor within the catheter senses the deflection (location and orientation) of the distal tip relative to the distal end of the insertion tube. Movement of the distal tip relative to the insertion tube is indicative of deformation of the resilient member, and thus gives an indication of the pressure.

SUMMARY OF THE INVENTION

An embodiment of the present invention provides a calibration apparatus including a fixture, a sensing device and a calibration processor. The fixture is coupled to accept a probe so that a distal tip of the probe presses against a point in the fixture and produces first measurements indicative of a deformation of the distal tip relative to a distal end of the probe, in response to pressure exerted on the distal tip. The sensing device is coupled to the fixture and is configured to produce second measurements of a mechanical force exerted by the distal tip against the point. The calibration processor is configured to receive the first measurements from the probe, to receive the second measurements from the sensing device and to compute, based on the first and second measurements, one or more calibration coefficients for assessing the pressure as a function of the first measurements.

In some embodiments, the fixture is coupled to cause the probe to press against the point at one or more predefined angles, and the calibration processor is configured to compute the calibration coefficients as a function of the predefined angles. The apparatus may include a dome covering the fixture, the dome having a plurality of insertion holes that are configured to direct the probe to the point at the predefined angles. Alternatively, the apparatus may include a receptacle configured to hold the distal end, a track coupled to the receptacle and configured to position the receptacle at multiple angles relative to the point, and a lift configured to raise the fixture so as to cause the distal tip to press against the point. The apparatus may include an input device coupled to the calibration processor and configured to accept the predefined angles.

In another embodiment, the fixture includes a cone-shaped cup. In yet another embodiment, the fixture holds the probe in a temperature-controlled liquid. In still another embodiment, the sensing device includes a load cell. In an embodiment, the calibration processor is configured to store the calibration coefficients in a memory that is coupled to the probe. The memory may include an Electronically Erasable Programmable Read Only Memory ($E^2$PROM).

There is also provided, in accordance with an embodiment of the present invention, a method of calibrating, including inserting a probe having a distal tip into a fixture, pressing the distal tip against a point in the fixture so as to cause a deformation of the distal tip relative to a distal end of the probe in response to pressure exerted on the distal tip, receiving from the probe first measurements indicative of the deformation, receiving from a sensing device coupled to the fixture second measurements indicative of a mechanical force exerted by the distal tip against the point, and computing, based on the first and second measurements, one or more calibration coefficients for assessing the pressure as a function of the first measurements.

BRIEF DESCRIPTION OF THE DRAWINGS

The disclosure is herein described, by way of example only, with reference to the accompanying drawings, wherein.

DETAILED DESCRIPTION OF EMBODIMENTS

Some invasive probes comprise pressure sensors for measuring the contact pressure between the probe and intra-body tissue. For example, the distal tip of a cardiac catheter may comprise a pressure sensor, which deforms in response to the pressure exerted by the distal tip on the endocardial tissue. A position sensor in the catheter measures the deflection of the distal tip, and thus provides an indication of the contact pressure. In many practical cases, however, the relationship between the actual contact pressure and the reading of the position sensor varies from one catheter to another.

In order to ensure accurate pressure measurements, embodiments of the present invention provide methods and systems for calibrating probes (e.g., catheters) fitted with pressure sensors. In some embodiments, a calibration apparatus comprises a fixture for accepting a catheter at a certain angle, and a sensing device (e.g., a load cell) for measuring the mechanical force exerted by the catheter against a given point in the fixture. When the catheter is inserted into the fixture at a given angle and pressed against the given point, the catheter produces deformation (e.g., deflection) measurements of its distal tip, and the sensing device produces force measurements.

In some embodiments, a calibration processor receives the deflection measurements from the catheter and the force measurements from the sensing device, and computes calibration coefficients for assessing the pressure exerted by the catheter as a function of the deflection measurements.

In some embodiments, the calibration is performed for different engagement angles between the catheter and the point in the fixture. In some embodiments, the calibration coefficients are stored in a non-volatile memory that is coupled to the catheter. When the catheter is later used in a medical system, the actual pressure exerted by the catheter's distal tip on the body tissue can be derived with high accuracy from the deflection measurements, using the calibration coefficients.

Figure 1:
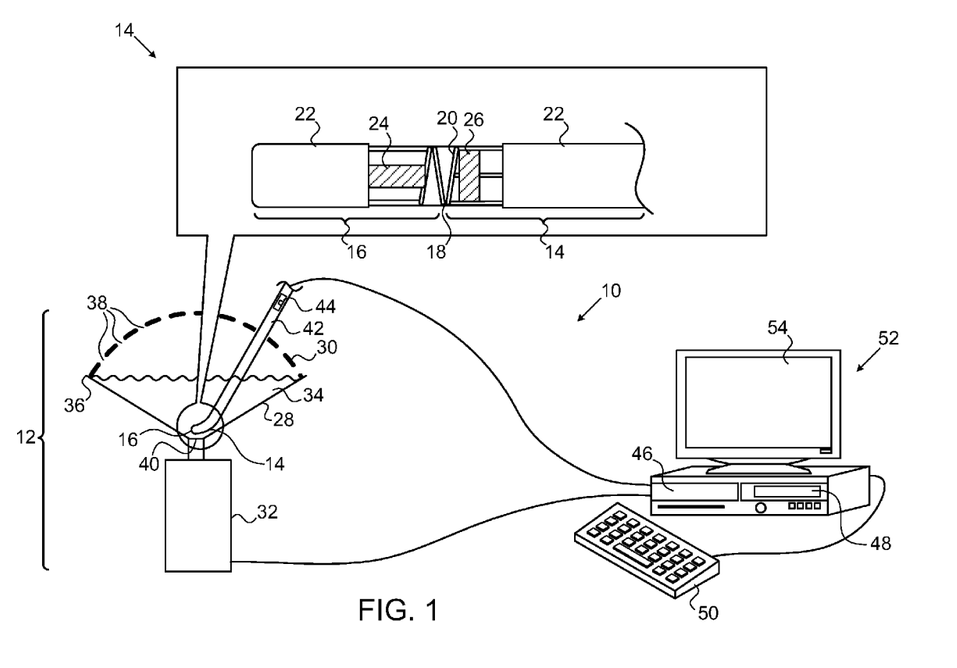
FIG. 1 is a schematic pictorial illustration of a calibration system for a pressure-sensitive catheter, in accordance with an embodiment of the present invention.

FIG. 1 is an illustration of a calibration system 10 for a pressure-sensitive catheter, in accordance with an embodiment of the present invention. System 10 comprises a calibration apparatus 12 coupled to a calibration unit 52. In the embodiment described hereinbelow, system 10 is used for calibrating a probe 42, in the present example a catheter for therapeutic and/or diagnostic purposes in a heart or in other body organs.

Probe 42 comprises a distal end 14, with a distal tip 16 connected to the distal end via a joint 18. Distal end 14 and distal tip 16 are both covered by a flexible, insulating material 22. The area of joint 18 is covered, as well, by a flexible, insulating material, which may be the same as material 22 or may be specially adapted to permit unimpeded bending and compression of the joint, (This material is cut away in FIG. 1 in order to expose the internal structure of the catheter.) Distal tip 16 is typically relatively rigid, by comparison with distal end 14.

Distal tip 16 is connected to distal end 14 by a resilient member 20. In FIG. 1, the resilient member has the form of a coil spring, but other types of resilient components may alternatively be used for this purpose. Resilient member 20 permits a limited range of relative movement between tip 16 and distal end 14 in response to forces exerted on the distal tip.

Distal tip 16 contains a magnetic position sensor 24. Sensor 24 may comprise one or more miniature coils, and typically comprises multiple coils oriented along different axes. Distal end 14 contains a miniature magnetic field generator 26 near resilient member 20. Typically, field generator 26 comprises a coil, which is driven by a current conveyed through the catheter from calibration unit 52. Alternatively, position sensor 24 may comprise either another type of magnetic sensor, an electrode which serves as a position transducer, or position transducers of other types, such as impedance-based or ultrasonic position sensors. Although FIG. 1 shows a probe with a single position sensor, embodiments of the present invention may utilize probes with more than one position sensors.

The magnetic field created by field generator 26 causes the coils in sensor 24 to generate electrical signals at the drive frequency of the field generator. The amplitudes of these signals will vary depending upon the location and orientation of distal tip 16 relative to distal end 14. A calibration processor 46 in calibration unit 52 processes these signals in order to determine the axial displacement and the magnitude of the angular deflection of the distal tip relative to distal end 14. (Because of the axial symmetry of the field generated by a coil, only the magnitude of the deflection can be detected using a single coil in field generator 26, and not the direction of the deflection. Optionally, field generator 26 may comprise two or more coils, in which case the direction of deflection may be determined, as well). The magnitudes of the displacement and deflection may be combined by vector addition to give a total magnitude of the movement of distal tip 16 relative to distal end 14.

The relative movement of distal tip 16 relative to distal end 14 gives a measure of the deformation of resilient member 20. Thus, the combination of field generator 26 with sensor 24 serves as a pressure sensing system. By virtue of the combined sensing of displacement and deflection, this pressure sensing system reads the pressure correctly regardless of whether the pressure is exerted on distal tip 16 head-on or at an angle. Further details of this sort of probe and position sensor are described in U.S. Patent Application Publications 2009/0093806 and 2009/0138007, cited above.

Probe 42 also comprises a non-volatile memory 44, such as electronically erasable programmable read only memory ($E^2PROM$), which stores calculation coefficients computed during calibration. As discussed supra, when the catheter is later used in a medical system, the actual pressure exerted by the catheter's distal tip on body tissue can be derived with high accuracy from deflection measurements, using the calibration coefficients stored in memory 44.

Calibration apparatus 12 comprises a fixture 28 that is configured to accept a probe to be calibrated. In the embodiment of FIG. 1, fixture 28 comprises a cup (e.g., a cone-shaped cup) having a top 36 and a base 40. In the present example, top 36 is wider than base 40. In alternative embodiments, fixtures having any other suitable mechanical configurations can also be used.

Fixture 28 may contain a temperature controlled liquid 34, which is held at a typical human body temperature (e.g., using a thermostat and a heating element). Using this technique, the calibration procedure of probe 42 is carried out at a temperature that closely resembles the operating temperature of the probe in the body. Temperature control may be important because the resiliency or other mechanical properties of elements of the probe may vary sharply with temperature. For example, joint 18 may contain elements such as a nickel titanium alloy (also referred to as NiTi or Nitinol) spring and a plastic outer covering (i.e., insulating material 22), whose resiliency may vary with the temperature of liquid 34.

To control the angle of engagement between catheter 42 and fixture 28, an operator (not shown) inserts the catheter into one of multiple insertion holes 38 in a dome 30 covering fixture 28. Each of the insertion holes may accept the catheter at a different angular position. The insertion holes are configured to direct distal tip 16 to press against a given point of fixture 28. In the configuration shown in FIG. 1, insertion holes 38 direct distal tip 16 to press against base 40.

In addition to fixture 28 and dome 30, calibration apparatus 12 comprises a load cell 32 coupled to base 40. The load cell measures the downward mechanical force exerted by the distal tip on base 40. Although the system shown in FIG. 1 measures the downwards force using load cell 32, system 10 may use any other suitable type of sensor to measure the downward force, and such sensors are thus considered to be within the spirit and scope of this invention.

Both load cell 32 and probe 42 are connected to calibration unit 52 via suitable interfaces (e.g., cables and connectors). Calibration unit 52 comprises calibration processor 46, a memory 48, a display 54 and an input device 50, such as a keyboard. Processor 46 typically comprises a general-purpose computer, with suitable front end and interface circuits for receiving signals from position sensor 24 and load cell 32, as well as for controlling the other components of calibration unit 52. Processor 46 may be programmed in software to carry out the functions that are described herein. The software may be downloaded to processor 46 in electronic form, over a network, for example, or it may be provided on tangible media, such as optical, magnetic or electronic memory media. Alternatively, some or all of the functions of processor 46 may be carried out by dedicated or programmable digital hardware components.

Figure 2:
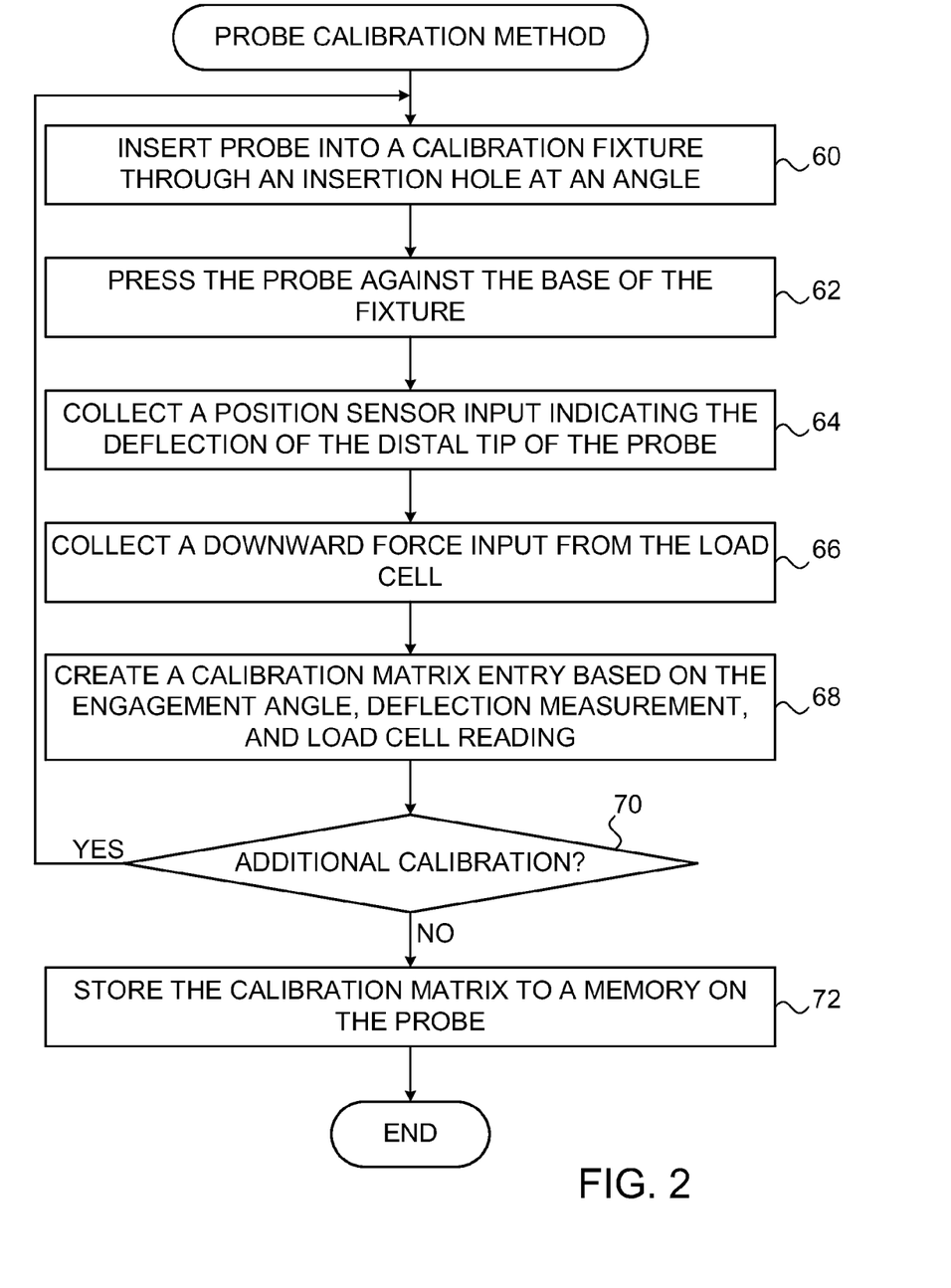
FIG. 2 is a flow diagram that schematically illustrates a method of calibrating a pressure-sensitive catheter, in accordance with an embodiment of the present invention.

FIG. 2 is a flow diagram that schematically illustrates a method of calibrating a pressure-sensitive catheter, in accordance with an embodiment of the present invention. To calibrate probe 42, the operator inserts the catheter into one of insertion holes 38 (step 60) and presses distal tip 16 against base 40 (step 62). The configuration of fixture 28 and dome 30 helps ensure that distal tip 16 will press against base (i.e., the same point of the fixture) regardless of which insertion hole is used for calibration. Typically, each insertion hole defines a different angle of engagement of the catheter with respect to base 40.

Pressing distal tip 16 against base 40 causes catheter 42 to bend at joint 18, thereby deflecting the distal tip. Position sensor 24 in distal tip 16 outputs a signal indicative of the deflection of the distal tip relative to distal end 14. Simultaneously, load cell 32 outputs a measurement indicative of the downward mechanical force exerted by distal tip 16 on base 40. Both the deflection and downward force measurements are sent to calibration unit 52, where the operator enters the engagement angle for this calibration step via keyboard 50.

In some embodiments, insertion holes 38 are labeled with respective identifiers. During the calibration process, the operator enters the identifier of the insertion hole being used into calibration unit 52 via input device 50. In an alternative embodiment, dome 30 may comprise one more proximity sensors, which automatically detect the insertion hole into which the catheter is inserted. When the operator inserts catheter 42 into one of the insertion holes, the proximity sensors will send electrical signals to calibration unit 52, and processor 46 will analyze the electrical signals to determine which of the insertion hole is being used. Any suitable type of proximity sensors, such as optical sensors or Hall-effect sensors, can be used.

Calibration unit 52 accepts the deflection measurement from sensor 24 in the probe (step 64), the downward force measurement from load cell 32 (step 66), and the angle of engagement from the operator. Based on these three inputs, processor 46 computes calibration coefficients for calibrating the deflection measurements of probe 42 (step 68). By mapping a position measurement from position sensor 24 against a force vector from load cell 32 at a given engagement angle, the calibration coefficient determines the force on distal tip 16 based on the position sensor measurements. In other words, a given calibration coefficient translates the deflection measurement of tip 16 into an actual pressure reading, for a given engagement angle.

If more calibration points are desired (step 70), then the method returns to step 60 above. Otherwise, processor 46 stores the calibration matrix to memory 44 on the probe (step 72), and the method terminates. In some embodiments, the operator may collect multiple data points for a given engagement angle (a given insertion hole 38) by exerting different amounts of pressure on the probe.

To store the calibration matrix, processor 46 may store an analytic calculation to memory 44 based on the computed coefficients. Alternatively, processor 46 may store a lookup table with inter-measurement interpolation to memory 44. In some embodiments, processor 46 may store a combination of the two (e.g., coefficients chosen according to a region) to memory 44.

Figure 3:
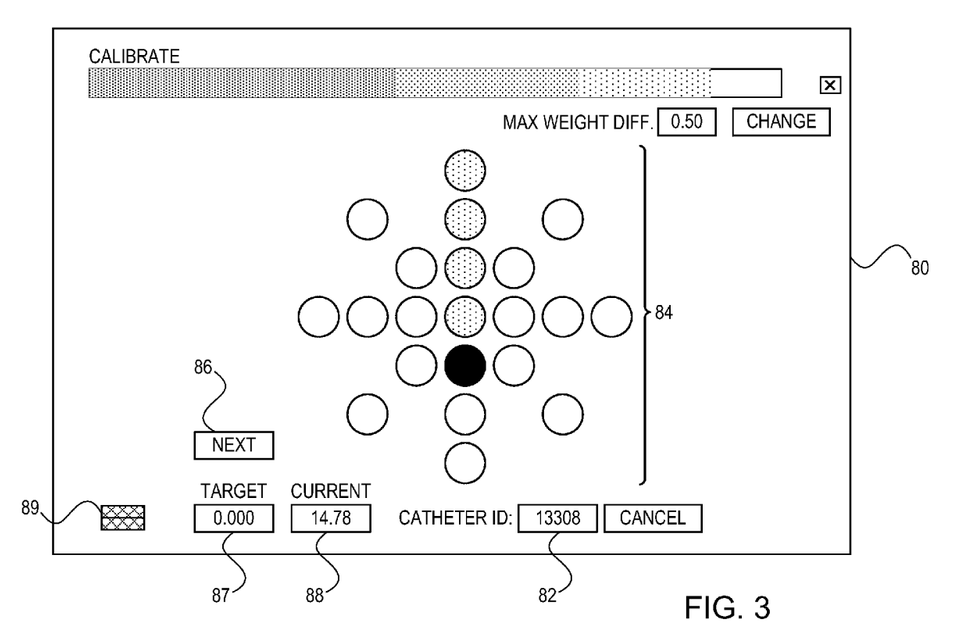
FIG. 3 is a schematic pictorial representation of a graphical user interface of a calibration system for a pressure-sensitive catheter, in accordance with an embodiment of the present invention.

FIG. 3 is a schematic representation of a graphical user interface (GUI) 80 operative to manage calibration of catheter 42, in accordance with an embodiment of the present invention. In this embodiment, display 54 presents GUI 80 to the operator. The operator enters the identity (e.g., a serial number) of the catheter being calibrated into a text box 82 using input device 50. GUI 80 presents a map 84 comprising a diagrammatical representation of insertion holes 38. Each of the insertion holes on the map is color coded to indicate its status during the calibration procedure. For example, in this embodiment, the insertion hole currently being used by the calibration procedure is black, the insertion holes previously used are gray, and the insertion holes not yet used are white. Returning to step 70 in FIG. 2, if additional calibration points are desired, the user presses a "Next" button 86 to identify the next insertion hole to be used in the calibration.

GUI 80 may comprise additional fields or features, such as text boxes 87 and 88 for displaying the target and actual pressure exerted on the catheter, respectively. A bar 89 on the left-hand side of the screen indicates the actual pressure. The GUI shown in FIG. 3 is chosen purely by way of example, and any other suitable GUI can also be used.

Figure 4:
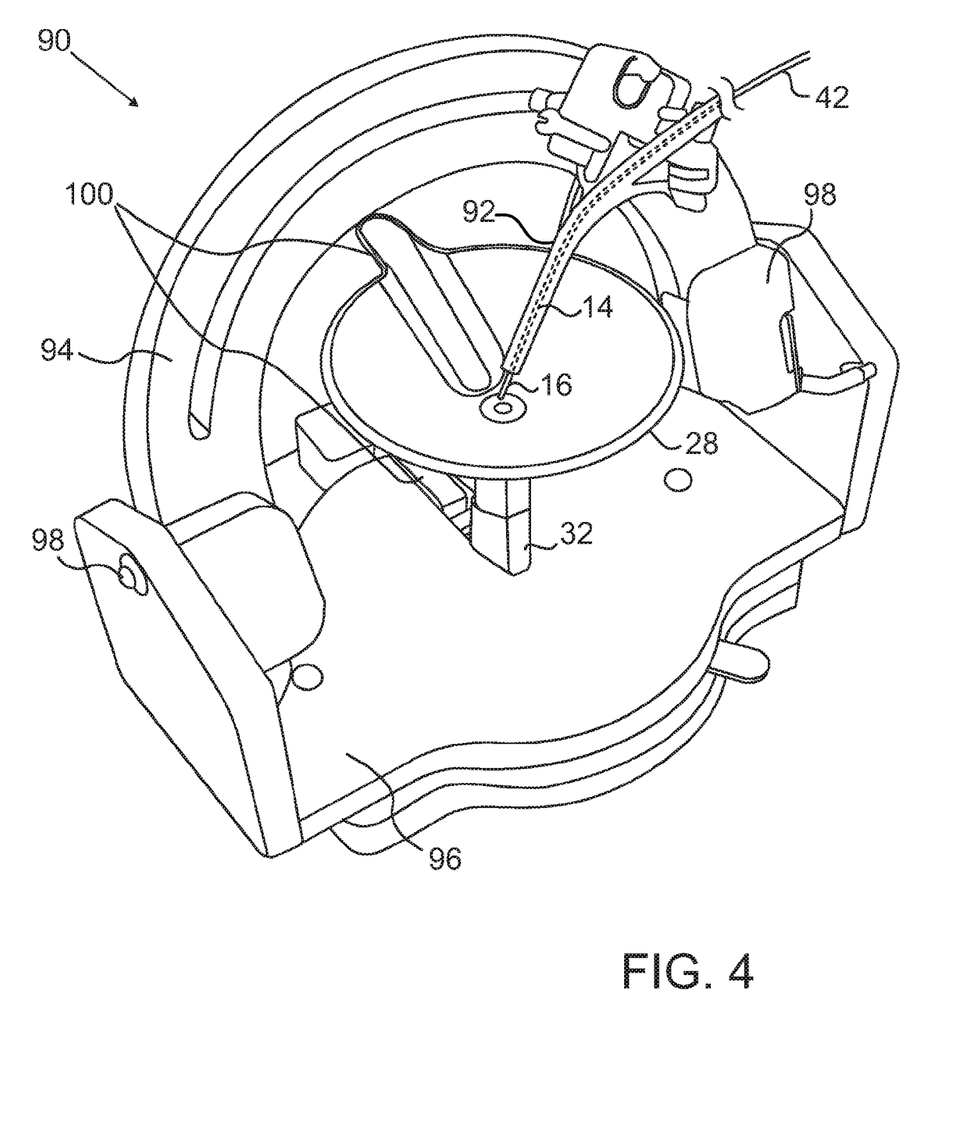
FIG. 4 is schematic pictorial illustration of a calibration system for a pressure-sensitive catheter, in accordance with an alternative embodiment of the present invention.

FIG. 4 is schematic pictorial illustration of a calibration system 90 for catheter 42, in accordance with an alternative embodiment of the present invention. In system 90, a receptacle 92 holds distal end 14, leaving distal tip 16 exposed at joint 18. The proximal end of receptacle 92 is coupled to a track 94. Track 94 is arch-shaped and is coupled to a stand 96 via joints 98. Joints 98 enable track 94 to be rotated in the stand. Positioning receptacle 92 along track 94 and rotating the track enables distal tip 16 to press against cup 28 at a variety of engagement angles. To deflect distal tip (i.e., since track 90 has motion limited to rotation, and the path of receptacle 92 is limited to the track), a lift 100 raises cup 28 and load cell 32, pressing the cup against distal tip 16. A load cell (not shown in the figure) is coupled to the lift and measures the pressure exerted on the catheter tip by the cup. When using the calibration setup of FIG. 4, calibration unit 52 operates similarly to its operation in the setup of FIG. 1 above.

Figure 5:
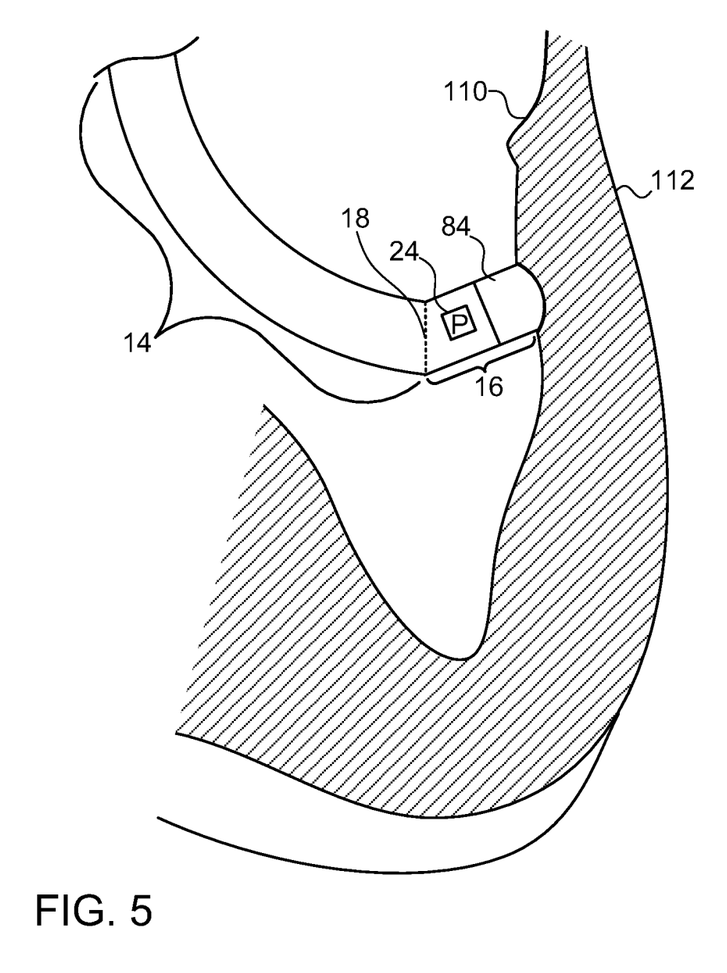
FIG. 5 is a schematic detail view showing the distal tip of a pressure-sensitive catheter in contact with endocardial tissue, in accordance with an embodiment of the present invention.

FIG. 5 is a schematic detail view showing distal tip 16 in contact with an endocardial tissue 110 of a heart 112, in accordance with an embodiment of the present invention. In the present example, tip 16 comprises an electrode 114. In some electrophysiological diagnostic and therapeutic procedures, such as intracardiac electrical mapping, it is important to maintain the proper level of force between electrode 114 and tissue 110. As a medical professional (not shown) presses distal tip 16 against endocardial tissue 110, the catheter bends at joint 18. Sufficient force is needed in order to ensure good electrode contact between the distal tip and the tissue. Poor electrical contact can result in inaccurate readings. On the other hand, excessive force can deform the tissue and thus distort the map.

When tip 16 presses against tissue 110, sensor 24 produces measurements that are indicative of the deflection of tip 16 with respect to distal end 14. The medical imaging system (e.g., mapping system—not shown) translates these measurements into accurate pressure readings using the calibration coefficients stored in memory 44 of the probe. Thus, calibration of the invasive probe using embodiments of the present invention ensures that the medical professional can accurately control the force exerted by the probe on the tissue.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It is intended that the appended claims cover all such features and advantages of the disclosure that fall within the spirit and scope of the present disclosure. As numerous modifications and changes will readily occur to those skilled in the art, it is intended that the disclosure not be limited to the limited number of embodiments described herein. Accordingly, it will be appreciated that all suitable variations, modifications and equivalents may be resorted to, falling within the spirit and scope of the present disclosure.

What is claimed is:

1. A calibration apparatus, comprising:
   a fixture, which is coupled to accept a probe so that a distal tip of the probe presses against a point in the fixture and produces first measurements indicative of a deformation of the distal tip relative to a distal end of the probe, in response to pressure exerted on the distal tip;
   a sensing device, which is coupled to the fixture and is configured to produce second measurements of a mechanical force exerted by the distal tip against the point; and
   a calibration processor, which is configured to receive the first measurements from the probe, to receive the second measurements from the sensing device and to compute, based on the first and second measurements, one or more calibration coefficients for assessing the pressure as a function of the first measurements.

2. The apparatus according to claim 1, wherein the fixture is coupled to cause the probe to press against the point at one or more predefined angles, and wherein the calibration processor is configured to compute the calibration coefficients as a function of the predefined angles.

3. The apparatus according to claim 2, and comprising a dome covering the fixture, the dome having a plurality of insertion holes that are configured to direct the probe to the point at the predefined angles.

4. The apparatus according to claim 2, and comprising a receptacle configured to hold the distal end, a track coupled to the receptacle and configured to position the receptacle at multiple angles relative to the point, and a lift configured to raise the fixture so as to cause the distal tip to press against the point.

5. The apparatus according to claim 2, and comprising an input device coupled to the calibration processor and configured to accept the predefined angles.

6. The apparatus according to claim 1, wherein the fixture comprises a cone-shaped cup.

7. The apparatus according to claim 1, wherein the fixture holds the probe in a temperature-controlled liquid.

8. The apparatus according to claim 1, wherein the sensing device comprises a load cell.

9. The apparatus according to claim 1, wherein the calibration processor is configured to store the calibration coefficients in a memory that is coupled to the probe.

10. The apparatus according to claim 9, wherein the memory comprises an Electronically Erasable Programmable Read Only Memory $E^2PROM$.

11. A method for calibration, comprising:
    inserting a probe having a distal tip into a fixture, and pressing the distal tip against a point in the fixture, so as to cause a deformation of the distal tip relative to a distal end of the probe in response to pressure exerted on the distal tip;
    receiving from the probe first measurements indicative of the deformation;
    receiving from a sensing device coupled to the fixture second measurements indicative of a mechanical force exerted by the distal tip against the point; and
    computing, based on the first and second measurements, one or more calibration coefficients for assessing the pressure as a function of the first measurements.

12. The method according to claim 11, wherein inserting the probe comprises causing the probe to press against the point at one or more predefined angles, and wherein computing the calibration coefficients comprises calculating the calibration coefficients as a function of the angles.

13. The method according to claim 12, wherein inserting the probe comprises placing the probe into one of a plurality of insertion holes in a dome covering the fixture, so as to direct the probe to the point at the predefined angles.

14. The method according to claim 12, wherein inserting the probe comprises holding the probe in a receptacle coupled to a track, so as to position the receptacle at one of multiple angles relative to the point, and raising the fixture in order for the distal tip to press against the point.

15. The method according to claim 11, wherein the fixture comprises a cone-shaped cup.

16. The method according to claim 11, wherein the fixture holds the probe in a temperature-controlled liquid.

17. The method according to claim 11, wherein the sensing device comprises a load cell.

18. The method according to claim 11, and comprising storing the calibration coefficients in a memory coupled to the probe.

19. The method according to claim 18, wherein the memory comprises an $E^2PROM$.

* * * * *